United States Patent
Rack et al.

(10) Patent No.: US 7,595,426 B2
(45) Date of Patent: Sep. 29, 2009

(54) METHOD FOR THE PRODUCTION OF 1,3,5-TRIFLUORO-2,4,6-TRICHLOROBENZENE FROM FLUOROBENZENE DERIVATIVES

(75) Inventors: Michael Rack, Heidelberg (DE); Sebastian Peer Smidt, Mannheim (DE); Manuel Budich, Böhl-Iggelheim (DE); Volker Maywald, Ludwigshafen (DE); Michael Keil, Freinsheim (DE); Bernd Wolf, Fußgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 164 days.

(21) Appl. No.: 11/911,971

(22) PCT Filed: Apr. 21, 2006

(86) PCT No.: PCT/EP2006/061766

§ 371 (c)(1), (2), (4) Date: Oct. 19, 2007

(87) PCT Pub. No.: WO2006/111583

PCT Pub. Date: Oct. 26, 2006

(65) Prior Publication Data

US 2008/0214878 A1    Sep. 4, 2008

(30) Foreign Application Priority Data

Apr. 22, 2005    (DE) .................. 10 2005 018 934

(51) Int. Cl.
*C07C 22/00* (2006.01)
*C07C 17/00* (2006.01)

(52) U.S. Cl. .................. 570/147; 570/155; 570/156

(58) Field of Classification Search ................ 570/147, 570/155, 156
See application file for complete search history.

(56) References Cited

U.S. PATENT DOCUMENTS

| | | | |
|---|---|---|---|
| 3,852,365 A | 12/1974 | Mahler | |
| 4,500,315 A | 2/1985 | Pieniak et al. | |
| 5,283,378 A | 2/1994 | Bielefeldt et al. | |
| 6,215,032 B1 | 4/2001 | Cheng et al. | |
| 6,265,627 B1 | 7/2001 | Igumnov et al. | |

FOREIGN PATENT DOCUMENTS

| | | |
|---|---|---|
| EP | 0 163 230 | 12/1985 |
| EP | 0 481 317 | 4/1992 |
| JP | 60-246327 | 12/1985 |
| JP | 04-224535 | 8/1992 |
| RU | 2084437 | 5/1995 |
| WO | WO 03/101926 | 12/2003 |

OTHER PUBLICATIONS

Riemschneider, Randolph, "Untersuchungen über den Halogen-Halogen-Austausch am aromatischen Kern, III", Chem. Ber., 1958, p. 2605-2608, vol. 91.
Shipilov, A. I. et al., "Catalytic Fluorination of Hexachlorobenzene with Supported Potassium Fluoride", Russian Journal of Appl. Chem. 2000, p. 556-557, vol. 73, No. 3.
Trukin, D.V. et al., "Dechlorination of Polychlorofluorobenzenes by the Action of the Reducing System $NiCl_2$-2,2'-Bipyridyl(or 1,10-Phenanthroline)-Zn-DMF-$H_2O$", Russian Journal of Appl. Chem. 2000, p. 132-133, vol. 36, No. 1.
Varma, P.S. et al., "Halogenation, Part XXIII. Halogenation of Fluorobenzene, *o-*, *m-* and *p-*Fluorotoluenes", J. Indian Chem. Soc. 1994, p. 112-116, vol. 21.

*Primary Examiner*—Jafar Parsa
(74) *Attorney, Agent, or Firm*—Brinks Hofer Gilson & Lione

(57) ABSTRACT

Method for the production of 1,3,5-trifluoro-2,4,6-trichlorobenzene from fluorobenzene comprising steps A) and B): A) chlorination of fluorobenzene derivatives of formula (II), in which X=fluorine of H, Z=nitro, bromo or chloro and n=0 or 1-4 and B) fluorination of the distillation residue and separation by distillation of the 1,3,5-trifluoro-2,4,6-trichlorobenzene thus produced.

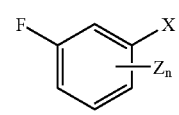

II

18 Claims, No Drawings

METHOD FOR THE PRODUCTION OF 1,3,5-TRIFLUORO-2,4,6-TRICHLOROBENZENE FROM FLUOROBENZENE DERIVATIVES

The present invention relates to a process for preparing 1,3,5-trifluoro-2,4,6-trichlorobenzene of the formula I

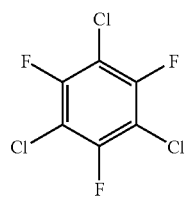

from fluorobenzene, which comprises the steps A) and B):
A) Chlorination of fluorobenzene of the formula II,

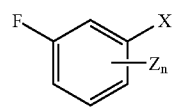

where X is fluorine or hydrogen, Z is nitro, bromine or chlorine and n is zero or 1-4, and
B) fluorination of the reaction products from step A and isolation of the resulting 1,3,5-trifluoro-2,4,6-trichlorobenzene of the formula I by distillation.

In addition, the invention relates to a process for preparing 1,3,5-trifluorobenzene by hydrodechlorination of the reaction product distilled off in step C) to form 1,3,5-trifluorobenzene.

It was an object of the present invention to provide an economical process which can be carried out on an industrial scale for preparing largely pure trifluorotrichlorobenzenes or trifluorobenzenes, which process avoids the liberation and handling of hexachlorobenzene.

We have accordingly found the process defined at the outset.

The individual reactions are known per se from the literature: J. Indian Chem. Soc. vol. 21, pp.112-14 (1944) teaches that chlorination of fluorobenzene in the presence of FeCl$_3$ as catalyst gives firstly 4-chlorofluorobenzene and when an excess of chlorine is used as isomer mixture of 2,4- and 3,4-dichlorofluorobenzene.

The chlorination of fluorobenzene with addition of Fe powder at 100° C. under UV illumination gives fluoropentachlorobenzene and, as main component, hexachlorobenzene. An analogous reaction with addition of AlCl$_3$ gives 1,2,4-trichlorofluorobenzene as main component in a yield of 8% [cf. Chem. Ber., vol. 91, pp.2605-7 (1958).

In U.S. Pat. Nos. 6,265,627, 6,215,032, RU 20 84 437 and Russ. J. of Appl. Chem., vol. 73, 3, pp. 522-23 (2000) describe the fluorination of hexachlorobenzene by means of KF using various catalysts. The process described sometimes give isomer mixtures.

JP 04224535 describes the dechlorination of 1,3-dichloro-2,4,6-trifluorobenzene by means of hydrogen in the presence of a palladium catalyst.

In Russ. J. of Org. Chem., vol. 36, 1, pp. 132-33 (2000) describes the dehalogenation of 1,3,5-trichlorotrifluorobenzene by means of zinc in the presence of NiCl$_2$ and bipyridine to give 1,3,5-trifluorobenzene.

The known processes have critical disadvantages for implementation on an industrial scale. Some of them start out from expensive starting materials, lead to isomer mixtures or require the handling of hexachlorobenzene which is classified as a POP (persistent organic pollutant) in the European Union. The handling of hexachlorobenzene should be avoided. Avoidance of this requires a large outlay in terms of apparatus. Hexachlorobenzene-free processes usually start out from relatively expensive starting materials. Complete avoidance of the by-product hexachlorobenzene in the chlorination of fluorobenzenes is possible only with considerable technical difficulty.

The syntheses described are therefore unsuitable for an industrial process for economic and practical reasons.

The process of the invention overcomes the disadvantages of the known processes in an elegant way. It starts out from readily available starting materials, uses readily available reagents and by-products formed are either recirculated to a renewed reaction or are converted into the end product during the course of the process.

The process of the invention enables the chlorination in step A) to be optimized so as to give a maximum yield of chlorofluorobenzene of the formula III without having to be concerned about formation of hexachlorobenzene which can be used as an alternative starting material to the chlorofluorobenzene of the formula IIII in the fluorination reaction.

In an embodiment of the process, steps A) and B) proceed without intermediate isolation of the reaction products of step A). The process is preferably carried out as a one-pot reaction.

If considerable amounts of underchlorinated by-products, i.e. compounds of the formula II in which Z is nitro or bromine and/or the index n is not 4, remain in the reaction solution after the chlorination, the reaction solution can be subjected to a distillation (step A2) to separate off the above-mentioned underchlorinated by-products.

In this case, step A) comprises two substeps A1) and A2) and the process of the invention is as follows:
A1) chlorination of fluorobenzene derivatives of the formula II

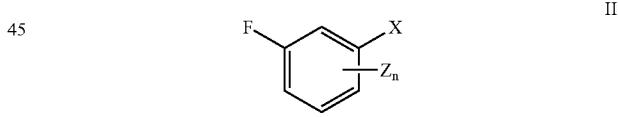

where X is fluorine or hydrogen, Z is nitro, bromine or chlorine and n is zero or 1-4,
A2) separation of volatile constituents from the reaction mixture comprising chlorofluorobenzene of the formula III

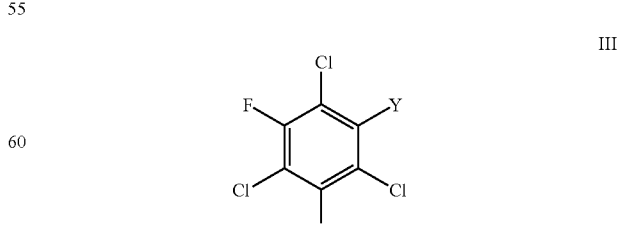

where Y is chlorine or fluorine, as main component by distillation,

B) fluorination of the distillation residue and isolation of the resulting 1,3,5-trifluoro-2,4,6,trichlorobenzene of the formula I by distillation.

Depending on the desired purity of the 1,3,5-trifluoro-2,4, 6-trichlorobenzene, this process variant comes into question when the proportion of underchlorinated by-products after the chlorination exceeds 1, 2 or up to 5% by weight.

In the process of the invention, products which have been underchlorinated in step A1) are separated off by distillation and recirculated for a renewed reaction in step A) or A1), while the overchlorinated product hexachlorobenzene formed by fluorine-chlorine exchange together with the main product chlorofluorobenzene of the formula III remain in the distillation bottoms and are fluorinated in step B) to give trichlorotrifluorobenzene of the formula I. Thus, the process of the invention produces no chlorinated hydrocarbons which have to be disposed of.

The chlorination in step A), or A1) is advantageously carried out using elemental chlorine at temperatures of from −10 to 50° C., preferably from −5 to 15° C., particularly preferably from +5 to 15° C., in the presence of Lewis acids such as Fe, $FeCl_3$, Al, $AlCl_3$, $SbCl_5$, $SbCl_3$, $BF_3$, $BF_3 \cdot OR_2$, where R is $C_1$-$C_4$-alkyl, $TiCl_4$, $SiCl_4$, $SnCl_4$, $ZnCl_2$, preferably $FeCl_3$ and $AlCl_3$, particularly preferably $AlCl_3$.

Suitable solvents are aliphatic hydrocarbons such as pentane, hexane, cyclohexane and petroleum ether, halogenated hydrocarbons such as methylene chloride, chloroform, carbon tetrachloride, 1,2-dichloroethane, trichloroethane and chlorobenzene, inorganic acids such as sulfuric acid and phosphoric acid, organic acids such as formic acid and acetic acid, and also dimethyl sulfoxide, dimethylformamide and dimethylacetamide (DMA), N-methylpyrrolidon (NMP), dimethylethyleneurea (DMEU) and dimethylpropyleneurea (DMPU), particularly preferably methylene chloride, chloroform, carbon tetrachloride, 1,2-dichloroethane and chlorobenzene. It is also possible to use mixtures of the solvents mentioned.

The Lewis acids are usually used in amounts of from 0.5 to 10 mol %.

The Lewis acid is preferably present in finely divided form.

As fluorobenzene derivative of the formula II it is possible to use, for example, fluorobenzene, m-difluorobenzene, o-fluoronitrobenzene, o-chlorofluorobenzene, m-fluoronitrobenzene, m-bromofluorobenzene, m-chlorofluorobenzene, 1-chloro-3-fluoro-2-nitrobenzene, 4-chloro-2-fluoro-1-nitrobenzene, 1-chloro-2-fluoro-3-nitrobenzene, p-fluoronitrobenzene, 1-chloro-2,4-difluorobenzene, 1-bromo-2,4-difluorobenzene, 2,4-difluoro-1-nitrobenzene, 1,3-difluoro-5-nitrobenzene, 1-bromo-3,5-difluorobenzene, 1-chloro-3,5-difluorobenzene, 1-chloro-2,4-difluoro-5-nitrobenzene, 2-chloro-1,3-difluoro-4-nitrobenzene. Preferred starting materials of the formula II are fluorobenzene, m-difluorobenzene, m-fluoronitrobenzene and m-chlorofluorobenzene.

If the process is carried out without the distillation step A2), the solvent from step A) is separated off by distillation after the chlorination is complete. The distillation residue comprising the reaction products is admixed with the solvent of step B) and the fluorinating agent. Residual water can subsequently be separated off by distillation, if appropriate at reduced pressure.

As a result of the distillation in step A2), the concentration of underchlorinated by-products is reduced; they can be passed as starting material of the formula II to a renewed reaction in step A) or A1). Any hexachlorobenzene formed remains as high-boiling component in the distillation bottoms and is available as starting material in the subsequent fluorination. In a preferred embodiment of the process, the reactor from step A), or A1), i.e. the distillation pot serves as reactor for the fluorination in step B).

The fluorination in step B) is preferably carried out by means of alkali metal fluorides and alkaline earth metal fluorides at temperatures of 100 to 300° C., preferably from 170 to 230° C., under anhydrous conditions in an inert organic solvent [cf. WO 03/101926; JP 60246327; EP 163 230; U.S. Pat. No. 4,500,315].

In a preferred embodiment, the fluorination product formed is distilled off during the reaction. This is preferably carried out under reduced pressure (vacuum distillation). The distillate has only a small proportion of isomeric trifluorotrichlorobenzenes.

Suitable alkali metal fluorides and alkaline earth metal fluorides are, for example, NaF, KF, CsF and $CaF_2$ in spray-dried or crystalline form. Preference is given to KF.

Suitable solvents are aliphatic hydrocarbons, aromatic hydrocarbons such as toluene, o-, m- and p-xylene, halogenated hydrocarbons such as chlorobenzene, and also dimethyl sulfoxide, dimethylformamide and DMA, carboxyamides, sulfolane, NMP, DMEU, DMPU, particularly preferably sulfolane, NMP, DMEU, DMPU. It is also possible to use mixtures of the solvents mentioned.

The reaction mixture can be dried in an elegant way by azeotropic distillation; preferred solvents are xylenes, toluene and chlorobenzene or mixtures thereof, in particular toluene.

The reaction is advantageously carried out in the presence of substoichiometric amounts of reduction inhibitors, particularly when using DMF or NMP as solvent. Possible reduction inhibitors are, for example, 1,3-dinitrobenzene, 1-chloro-3-nitrobenzene or 4-chloronitrobenzene.

In one embodiment of the process, step B) is carried out in the presence of a catalyst.

Catalysts for the halex reaction are known per se [cf.: WO 03/101926]; preference is given to quaternary ammonium and phosphonium salts such as those of the formulae Va, Vb and Vc:

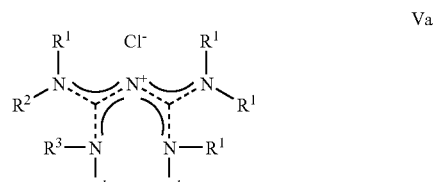

Va

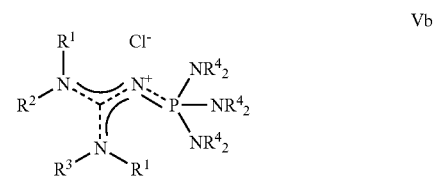

Vb

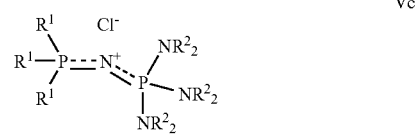

Vc where $R^1=C_1$-$C_4$-alkyl, $R^2$ and $R^3$ together form —$CH_2$—$CH_2$— or —$CH_2$—$CH_2$—$CH_2$— and $R^4=C_1$-$C_4$-alkyl. The following catalysts, in particular, are usually employed for halex reactions:

benzyl tributyl ammonium bromide; benzyl tributyl ammonium chloride; benzyl triethyl ammonium bromide; benzyl triethyl ammonium chloride; benzyl trimethyl ammonium chloride; cetyl pyridinium bromide; cetyl pyridinium chloride; cetyl trimethyl ammonium bromide; didecyl dimethyl ammonium chloride; dimethyl distearyl ammonium bisulfate; dimethyl distearyl ammonium methosulfate; dodecyl trimethyl ammonium bromide; dodecyl trimethyl ammonium chloride; methyl tributyl ammonium chloride; methyl tributyl ammonium hydr. sulfate; methyl tricaprylyl ammonium chloride; methyl trioctyl ammonium chloride; myristyl trimethyl ammonium bromide; phenyl trimethyl ammonium chloride; tetrabutyl ammonium borohydride; tetrabutyl ammonium bromide; tetrabutyl ammonium chloride; tetrabutyl ammonium fluoride; tetrabutyl ammonium hydrogensulfate; tetrabutyl ammonium hydroxide; tetrabutyl ammonium iodide; tetrabutyl ammonium perchlorate; tetraethyl ammonium bromide; tetraethyl ammonium chloride; tetraethyl ammonium hydroxide; tetrahexyl ammonium bromide; tetrahexyl ammonium iodide; tetramethyl ammonium bromide; tetramethyl ammonium chloride; tetramethyl ammonium fluoride; tetramethyl ammonium hydroxide; tetramethyl ammonium iodide; tetraoctyl ammonium bromide; tetrapropyl ammonium bromide; tetrapropyl ammonium chloride; tetrapropyl ammonium hydroxide; tributyl methyl ammonium chloride; triethyl benzyl ammonium chloride; hexa-$C_1$-$C_6$-alkylguanidinium chlorides and bromides;

quaternary phosphonium salts:

Benzyltriphenylphosphonium bromide; benzyltriphenylphosphonium chloride; butyltriphenylphosphonium bromide; butyltriphenylphosphonium chloride; ethyltriphenylphosphonium acetate; ethyltriphenylphosphonium bromide; ethyltriphenylphosphonium iodide; methyltriphenylphosphonium bromide; tetrabutylphosphonium bromide; tetraphenylphosphonium bromide; tetrakisdiethylaminophosphonium bromide;

polyglycols and crown ethers:

18-crown-6; Aliplex DB1860®; butyl diglyme; dibenzo-18-crown-6; diethylene glycol dibutyl ether; diethylene glycol dimethyl ether; diglyme; dipropylene glycol dimethyl ether; monoglyme; polyethylene glycol dibutyl ether; polyglycol BB 300®; polyglycol DME 200®; polyglycol DME 250®; polyglycol DME 500®; polyglycol DME 1000®; polyglycol DME 20000®; monoethylene glycol dimethyl ether; tetraethylene glycol dimethyl ether; tetraglyme; triethylene glycol dimethyl ether; and triglyme.

It is also possible to use mixtures of catalysts.

If step B) is carried out in a water-miscible solvent, the solvent can be separated off by addition of water, as a result of which the reaction product, above the melting point, separates as organic phase from the solvent mixture. The product can be isolated by phase separation and, if appropriate, subsequently freed of solvent residues by washing with water.

In a preferred embodiment of the process, the reaction product which has been distilled off in step B) is hydrodechlorinated without further purification to form trifluorobenzene (step C).

The hydrodechlorination in step C) is usually carried out at temperatures of from 50° C. to 150° C., preferably from 90° C. to 120° C. or from 110° C. to 140° C., in water or an inert organic solvent in the presence of a base [cf. JP 04224535].

Suitable solvents are water, alcohols such as methanol, ethanol, n-propanol, isopropanol, n-butanol and tert-butanol, and also dimethyl sulfoxide, dimethylformamide and dimethylacetamide, carboxylic acids such as formic acid and acetic acid, preferably water and acetic acid, in particular water. It is also possible to use mixtures of the solvents mentioned.

As bases, it is generally possible to use inorganic compounds such as alkali metal hydroxides and alkaline earth metal hydroxides, e.g. lithium hydroxide, sodium hydroxide, potassium hydroxide and calcium hydroxide, alkali metal oxides and alkaline earth metal oxides, e.g. lithium oxide, sodium oxide, calcium oxide and magnesium oxide, alkali metal hydrides and alkaline earth metal hydrides, e.g. lithium hydride, sodium hydride, potassium hydride and calcium hydride, alkali metal amides such as lithium amide, sodium amide and potassium amide, alkali metal carbonates and alkaline earth metal carbonates, e.g. lithium carbonate, potassium carbonate and calcium carbonate, and also alkali metal hydrogencarbonates such as sodium hydrogen carbonate, alkali metal acetates such as sodium acetate and potassium acetate and also alkali metal alcoxides and alkaline earth metal alcoxides, e.g. sodium methoxide, sodium ethoxide, potassium ethoxide, potassium tert-butoxide and dimethoxymagnesium, also organic bases, e.g. tertiary amines such as trimethylamine, triethylamine, tri-isopropylethylamine and N-methylpiperidine, pyridine, substituted pyridines such as collidine, lutidine and 4-dimethylaminopyridine, and also bicyclic amines. Particular preference is given to sodium acetate, potassium acetate, sodium hydroxide and potassium hydroxide.

The bases are generally used in an equimolar amount, in excess or, if appropriate, as solvents. Preference is given to using 3-4 molar equivalents, based on fluorochlorobenzene.

If the reaction is carried out in an aqueous solvent or solvent mixture, a pH of the reaction solution of from 1 to 7, in particular from 4 to 6, is preferred. The reaction can also be carried out in a buffer system.

The course of the reactions described, in particular the heterogeneous reactions, is favored by very intensive mixing of the reaction solutions. This applies particularly to step C). Single-stage or multistage disk stirrers, propeller stirrers and/or inclined blade stirrers and/or the installation of baffles in the reactor usually ensure intensive mixing of the reaction solution. A combination of various types of stirrer can also prove to be advantageous. The optimal stirrer geometry depends on the dimensions of the reactors used. The way in which gas is introduced is also dependent on the reactor geometry. A person skilled in the art will be familiar with methods of ensuring introduction of very finely divided gas.

The reaction is preferably carried out in the presence of a catalyst such as a transition metal catalyst, in particular Pd/C, Pt/C and Raney Ni or a mixture thereof.

In one embodiment of the process, the dechlorinated reaction products are distilled off continuously during the reaction. In this embodiment, the reaction proceeds satisfactorily even without a catalyst.

It is possible to carry out the process of the invention as a one-pot reaction, i.e. the process steps A) to B), or A1), A2) and B) are carried out in the same reactor. Any hexachlorobenzene formed in step A) or A1) remains in the reactor and is eliminated in the same reactor by means of the fluorination in step B).

The process of the invention comprising the steps A) to C) represents an elegant route which can be carried out on an industrial scale to largely pure trifluorobenzenes.

The 1,3,5-trichloro-2,4,6-trifluorobenzene and 1,3,5-trifluorobenzene obtainable by the process of the invention are suitable as intermediates for the production of dyes or active compounds in the pharmaceutical or agrochemical sector.

PROCESS EXAMPLES

Steps A1-A2)

Example 1

Preparation of 1-fluoro-2,3,4,5,6-pentachlorobenzene

A solution of 400 g (4.17 mol) of fluorobenzene in 2 l of 1,2-dichlorethane was admixed with 53.2 g (0.417 mol) of powdered $AlCl_3$. 1394 g of chlorine gas were subsequently passed into the solution at 0-5° C. After the end of the reaction, the HCl formed was driven out at about 20-25° C. by means of a stream of nitrogen. The reaction solution was admixed with 200 ml of water while stirring vigorously, and the phases were then separated at 50° C.

The organic phase comprised, according to analysis by gas chromatography (GC), 43.9% of fluoropentachlorobenzene, 36.2% of fluorotetrachlorobenzenes, 13.4% of fluorotrichlorobenzenes as main components and also further components in the percentage range. After vacuum distillation (140-145° C., 20 mbar), 86.2% of fluoropentachlorobenzene, 3% of fluorotetrachlorobenzenes, 3.3% of pentachlorobenzene and 2.5% of hexachlorobenzene remained in the bottoms according to GC. This mixture was used in the fluorination without further purification.

Example 2

Preparation of 1,3-difluoro-2,4,5,6-tetrachlorobenzene

A solution of 100 g (0.88 mol) of 1,3-difluorobenzene in 1 l of 1,2-dichloroethane was admixed with 11.7 g (0.088 mol) of powdered $AlCl_3$. 290 g of chlorine gas were subsequently passed into the solution at 0-5° C. After the end of the reaction, the HCl formed were driven out at about 20-25° C. by means of a stream of nitrogen, and the solution was filtered through silica gel. According to analysis by gas chromatography, the solution comprised 38.5% of dichlorodifluorobenzene, 33.6% of difluorotrichlorobenzenes, 14.5% of difluorotetrachlorobenzene as main components and also further components in the percentage range. A vacuum distillation gave, at 0.2 mbar in the temperature range 50-90° C., 60 g of a fraction comprising the title compound.

Step A)

Example 3

Preparation of Pentachlorofluorobenzene

A solution of 144 g (1.5 mol) of fluorobenzene in 1080 ml of 1,2-dichloroethane was admixed with 10 g (0.075 mol) of powdered $AlCl_3$, and 586 g of chlorine gas were then passed into the mixture at 5-15° C. The solution was then stirred at 25° C. for about 5 hours, then heated to 65° C. and 100 ml of water were subsequently added while stirring vigorously. At this temperature, the phases were separated and the organic phase was extracted with water. The solvent was distilled off and the residue was taken up in 1300 g of NMP. After gas-chromatographic analysis (GC), the yield was calculated as: 93.9% of pentachlorofluorobenzene, 4.9% of hexachlorobenzene and 1.1% of tetrachlorofluorobenzenes. The solution can directly be reacted further as described in example 6.

Step B)

Example 4

Preparation of 1,3,5-trichloro-2,4,6-trifluorobenzene from 1-fluoro-2,3,4,5,6-pentachlorobenzene 8.9 g of KF were suspended in 20 g of the distillation residue from example 1 (composition according to GC: 85.2% of fluoropentachlorobenzene, 11% of fluorotetrachlorobenzenes, 3.8% of hexachlorobenzene) and diluted with 50 ml of DMEU. The suspension was stirred at 220° C. in a pressure vessel for 12 hours. After depressurization, the contents were taken up in 100 ml of methyl tert-butyl ether (MTBE), washed with water, dried and the solvent was subsequently distilled off under reduced pressure. This gave 14.6 g of an isomer mixture which, according to GC, comprised 24% of the title compound.

Example 5

Preparation of 1,3,5-trichloro-2,4,6-trifluorobenzene from 1,3-difluoro-2,4,5,6-tetrachlorobenzene 2.8 g of KF and 0.6 g (2.12 mmol) of $(Et_2N)_4PBr$ were suspended in 10 g of the fraction from example 2, and the suspension was stirred at 180° C. in a pressure vessel for 24 hours. After depressurization, the product was taken up in 100 ml of $CH_2Cl_2$, washed with water, dried and the solvent was subsequently distilled off under reduced pressure. This gave 8.7 g of an isomer mixture comprising 45% (GC) of the title compound.

Example 6

Preparation of 1,3,5-trichlorotrifluorobenzene

A solution prepared in a manner analogous to example 3 (23.2% of fluoropenta-chlorobenzene in NMP) was admixed with 57 g (0.98 mol) of KF, 1.7 g of 1,3-dinitrobenzene and 299 g of NMP. To dry the solution, 100 g of NMP were distilled off at 81° C. and 10 mbar. A vacuum of 540 mbar was subsequently applied and the internal temperature was increased to 180° C. The crude product/NMP mixture was distilled off over a period of 16 hours. The distillate was washed twice with 250 g of water at 70° C. This gave 70.9 g of a mixture of trichlorotrifluorobenzene (75.6% of theory). 61.5% of 1,3,5-trichlorotrifluorobenzene were identified as main constituent.

Example 7

Preparation of 1,3,5-trichloro-2,4,6-trifluorobenzene from Fluorochlorobenzene Mixtures 74.4 g of the distillation residue from steps A1)-A2) having the composition (GC) 81.6% of fluoropentachlorobenzene, 4.5% of fluorotetrachlorobenzenes, 10.8% of hexachlorobenzene, together with 49 g of KF and 1.3 g of 1,3-dinitrobenzene were suspended in 400 g of NMP and 75 g of toluene. The mixture was dried azeotropically by distilling off the toluene under atmospheric pressure. A vacuum of 580 mbar was subsequently applied and the internal temperature was increased to 190° C. The reaction product distilled off over a period of 14 hours. The distillate was taken up in MTBE, washed with water and dried. Distilling off the solvent left 23.9 g of a residue which comprised 73.6% (GC) of the title compound.

Example 8

Preparation of 1,3,5-trichloro-2,4,6-trifluorobenzene from Fluorochlorobenzene Mixtures Example 7 was repeated using 100 g of a distillation residue from steps A1)-A2) having the composition (GC) 86.2% of fluoropentachlorobenzene, 3.0% of fluorotetrachlorobenzenes, 2.6% of hexachlorobenzene and 79.4 g of KF as fluorinating agent. This gave 47.6 g (52.6% of theory) of the title compound having a mp. of 65° C. The purity was >95% (determined by $^{19}$F-NMR) $^{19}$F-NMR (DMSO-D$_6$): δ=−113.6 ppm (s).

Example 9

Preparation of 1,3,5-trichloro-2,4,6-trifluorobenzene from Fluorochlorobenzene Mixtures The procedure of example 7 was repeated using 100 g of a distillation residue from steps A1)-A2) having the composition (GC) 86.2% of fluoropentachlorobenzene, 3.0% of fluorotetrachlorobenzenes, 2.6% of hexachlorobenzene and 79.4 g of KF as fluorinating agent in DMEU. This gave 30.2 g (33% of theory) of the title compound having a mp. of 65° C. The purity was >95% ($^{19}$F-NMR).

Example 10

Preparation of 1,3,5-trifluorobenzene

Palladium on carbon (10%, 410 mg), 100 g of water, 21.8 g of 1,3,5-trichloro-2,4,6-trifluorobenzene and 32.9 g of sodium acetate (4.5 equivalents) were placed in a pressure vessel. After flushing with nitrogen, the pressure vessel was heated to 140° C. and pressurized with 12 bar of hydrogen. A hydrogen pressure of 12 bar was maintained at 140° C. for about 12 hours while stirring vigorously. After cooling to 20-25° C., the pressure vessel was depressurized. The two-phase reaction solution was filtered and the phases were then separated. This gave a yield of 88.2% of 1,3,5-trifluorobenzene.

Step C)

Example 11

Hydrodechlorination of 1,3,5-trichloro-2,4,6-trifluorobenzene

Palladium on carbon (10%, 300 mg), aqueous sodium hydroxide solution (35% strength, 26.5 g, 232 mmol, 3.7 equivalents), 62 g of water and 1,3,5-trichloro-2,4,6-trifluorobenzene (15 g, 62 mmol) were placed in a pressure vessel. After flushing with nitrogen, the pressure vessel was heated to 140° C. and pressurized with 30 bar of hydrogen. A hydrogen pressure of 30 bar was maintained at 140° C. for 12 hours. After cooling to 20-25° C., the pressure vessel was depressurized. The reaction solution was subjected to an azeotropic distillation via a distillation attachment; the distillate went over at a temperature of 99.5° C. After separation of the phases, the lower organic phase comprised the title compound. Washing with water and drying gave 8.05 g of 1,3,5-trifluorobenzene (98% of theory).

Example 12

Hydrodechlorination of Trichlorotrifluorobenzene Mixture

Palladium on carbon (10%, 850 mg), 130 g of water, 50 g of a mixture of trichlorotrifluorobenzenes (1,3,5: 1,2,3: 1,2,4 isomers=69.1%: 21.7%: 9.2%) and 60 g of sodium acetate (4 equivalents) were placed in a pressure vessel. After flushing with nitrogen, the pressure vessel was heated to 140° C. and pressurized with 12 bar of hydrogen. A hydrogen pressure of 12 bar was maintained at 140° C. for 6 hours while stirring vigorously. After cooling to 20-25° C., the pressure vessel was depressurized. The two-phase reaction solution was filtered and the phases were then separated. This gave a yield of 91.3% of trifluorobenzenes.

The invention claimed is:

1. A process for preparing 1,3,5-trifluoro-2,4,6-trichlorobenzene from fluorobenzene, which comprises the steps A) and B):

A) Chlorination of fluorobenzene of the formula II,

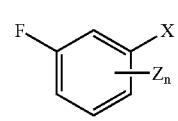

where X is fluorine or hydrogen, Z is nitro, bromine or chlorine and n is zero or 1-4, and B) fluorination of the reaction products from step A) and isolation of the resulting 1,3,5-trifluoro-2,4,6-trichlorobenzene by distillation.

2. The process according to claim 1, wherein the reaction product of the process according to claim 1 is subjected to a hydrodechlorination to form 1,3,5-trifluorobenzene in a step C.

3. The process according to claim 1 starting out from fluorobenzene of the formula II in which X is hydrogen and n is zero.

4. The process according to claim 1 starting out from 1,3-difluorobenzene of the formula II in which X is fluorine and n is zero.

5. The process according to claim 1, wherein the chlorination in step A) is carried out using elemental chlorine in the presence of AlCl$_3$.

6. The process according to claim 1, wherein, in step A), the chlorination A1) of fluorobenzene of the formula II is followed by a distillation step A2) to separate volatile constituents from the reaction mixture comprising chlorofluorobenzene of the formula III

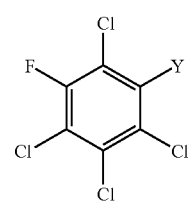

where Y is chlorine or fluorine, as main component.

7. The process according to claim 6, wherein fluorobenzenes having a low degree of chlorination are separated off by distillation in step A2) and are recirculated.

8. The process according to claim 1, wherein the fluorination in step B) is carried out using KF in the presence of a solvent.

9. The process according to claim 1, wherein the fluorination in step B) is carried out in the presence of a phase transfer catalyst.

10. The process according to claim 8, wherein the fluorination is carried out in the presence of a reduction inhibitor.

11. The process according to claim 1, wherein the steps A) and B) are carried out as a one-pot process.

12. The process according to claim 2, wherein the hydrodechlorination in step C) is carried out under pressure in the presence of a heterogenous catalyst and a base.

13. The process according to claim 2 starting out from fluorobenzene of the formula II in which X is hydrogen and n is zero.

14. The process according to claim 2 starting out from 1,3-difluorobenzene of the formula II in which X is fluorine and n is zero.

15. The process according to claim 9, wherein the fluorination is carried out in the presence of a reduction inhibitor.

16. The process according to claim 2, wherein the chlorination in step A) is carried out using elemental chlorine in the presence of $AlCl_3$.

17. The process according to claim 2, wherein, in step A), the chlorination A1) of fluorobenzene of the formula II is followed by a distillation step A2) to separate volatile constituents from the reaction mixture comprising chlorofluorobenzene of the formula III

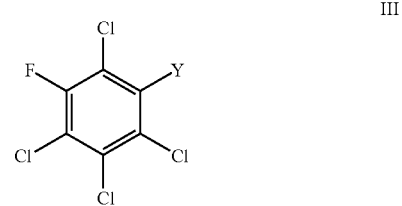

where Y is chlorine or fluorine, as main component.

18. The process according to claim 17, wherein fluorobenzenes having a low degree of chlorination are separated off by distillation in step A2) and are recirculated.

* * * * *